United States Patent [19]

Bowman et al.

[11] Patent Number: 4,736,850
[45] Date of Patent: Apr. 12, 1988

[54] ENDOTHELIAL CELL HARVESTING KIT

[75] Inventors: Phillip B. Bowman, Richmond, Calif.; David M. Workinger, Mesa; John L. Fisher, Flagstaff, both of Ariz.

[73] Assignee: W. L. Gore & Associates, Inc., Newark, Del.

[21] Appl. No.: 920,206

[22] Filed: Oct. 17, 1986

[51] Int. Cl.⁴ .......................... B65D 85/20; A61F 2/02
[52] U.S. Cl. ..................................... 206/570; 128/1 R; 206/370; 206/438; 206/514; 206/564
[58] Field of Search .............. 128/1 R, 749, 750; 206/363, 370, 438, 514, 518, 569, 570, 803, 828, 564, 372, 373; 220/408, 410

[56] References Cited

U.S. PATENT DOCUMENTS

| | | | |
|---|---|---|---|
| 2,980,280 | 4/1961 | Herlow | 206/514 |
| 3,777,882 | 12/1973 | McIntyre | 206/370 |
| 3,797,652 | 3/1974 | Chesky | 206/438 |
| 3,802,555 | 4/1974 | Grasty et al. | 206/370 |
| 3,916,874 | 11/1975 | Perrin | 128/1 R |
| 4,085,845 | 4/1978 | Perfect | 206/363 |
| 4,232,659 | 11/1980 | Dale | 128/1 R |
| 4,353,694 | 10/1982 | Pelerin | 206/370 |
| 4,501,363 | 2/1985 | Isbey, Jr. | 206/570 |
| 4,595,102 | 6/1986 | Cianci et al. | 206/370 |
| 4,643,303 | 2/1987 | Arp et al. | 206/370 |

FOREIGN PATENT DOCUMENTS 2132587 7/1984 United Kingdom ............... 206/828

Primary Examiner—Jimmy G. Foster
Attorney, Agent, or Firm—Mortenson & Uebler

[57] ABSTRACT

A cell harvesting kit and a method for harvesting cells from a vein of a patient are provided. The cell harvesting kit has a packaging container containing three trays, a support holding the components needed for cell harvesting, and three vials containing enzyme solutions and salt solution, respectively. The three trays include an outer tray having a lid engaged with the outer tray to preserve sterility, a component tray within the outer tray, the component tray having a sealed lid and having a shelf about its perimeter for supporting a support member having depressions therein for holding the components needed in cell harvesting, and a third tray contained within the component tray, the third tray comprising a process tray with a trough in which an excised vein may be placed for harvesting.

A method for harvesting cells from a vein of a patient is also provided.

3 Claims, 5 Drawing Sheets

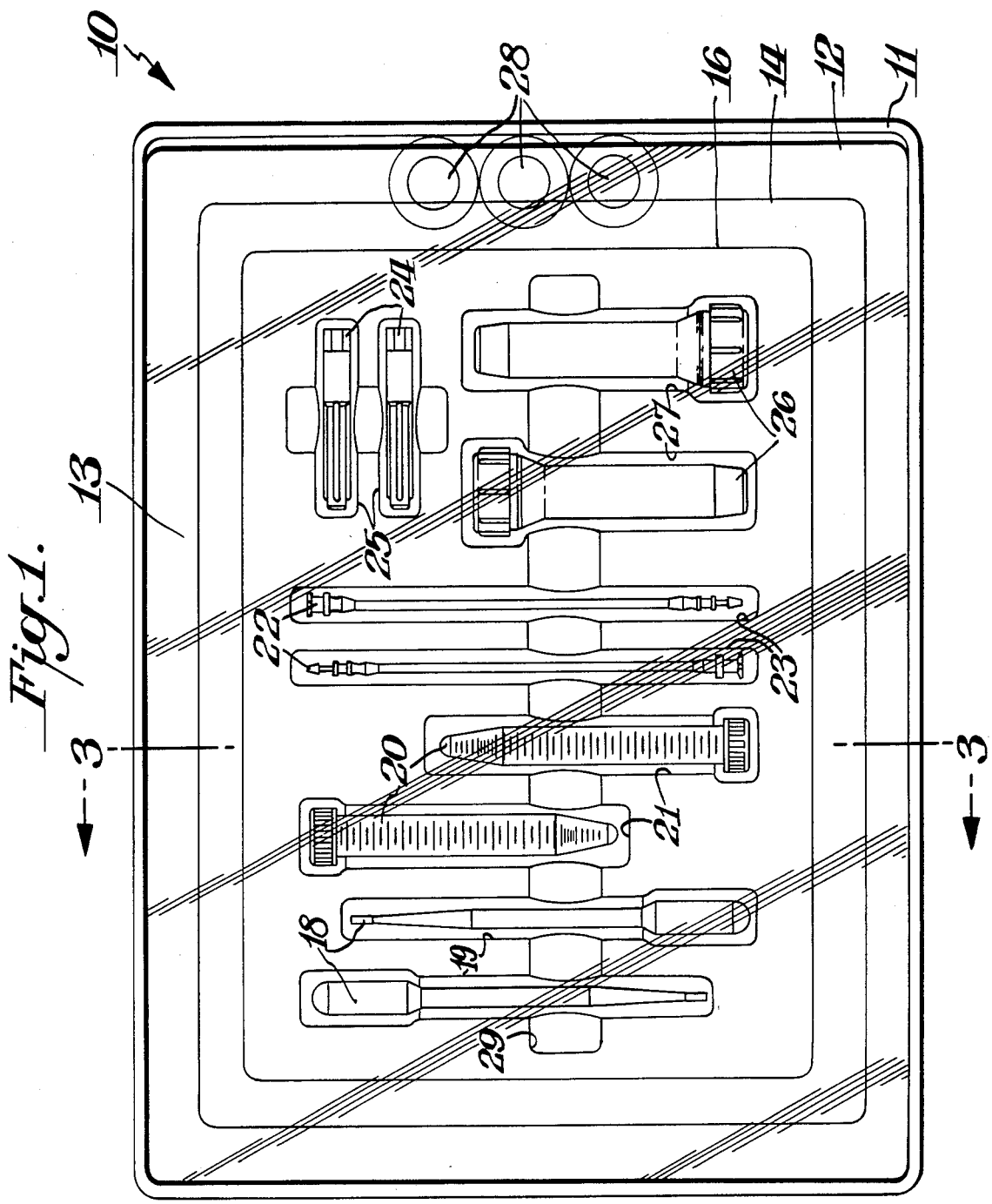

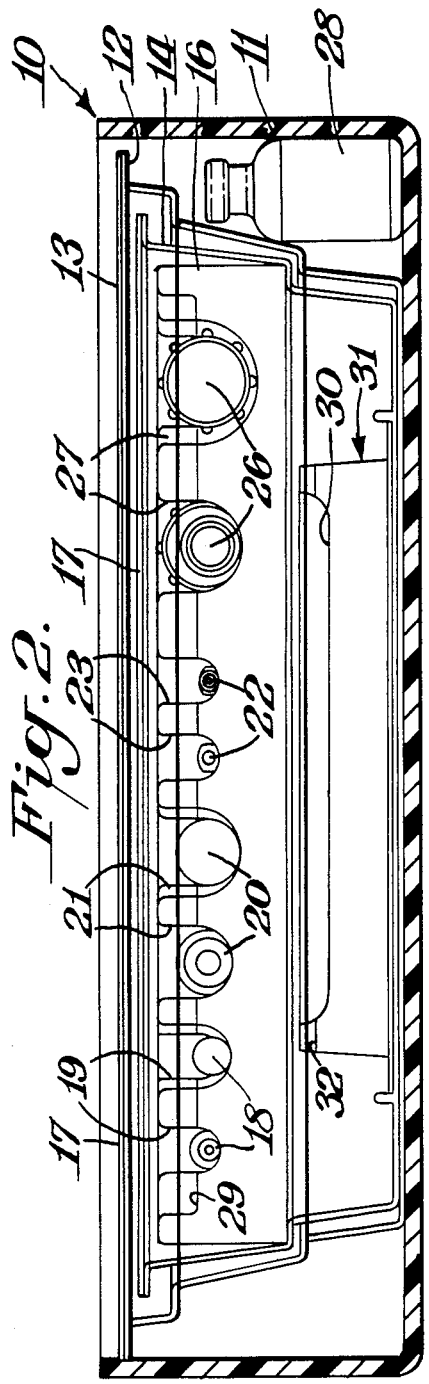
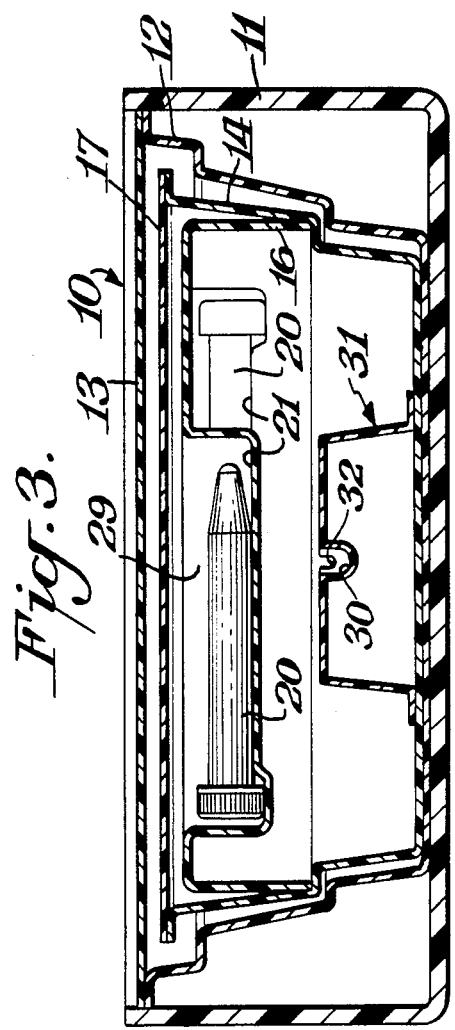

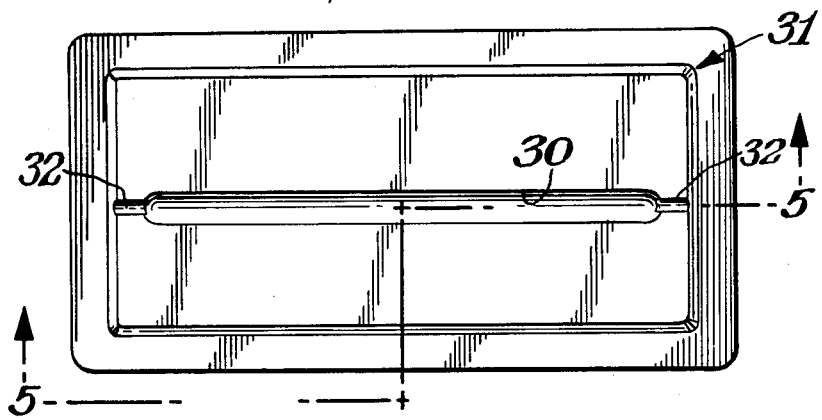
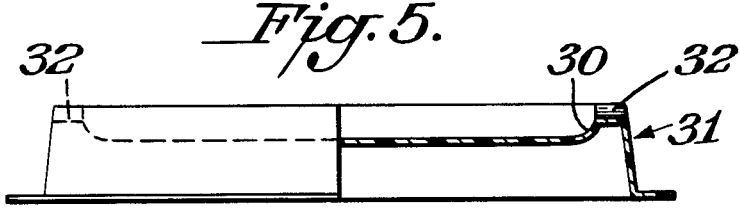 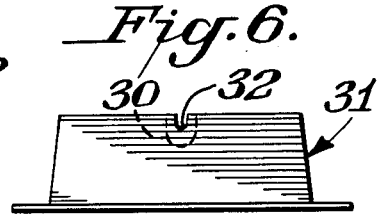
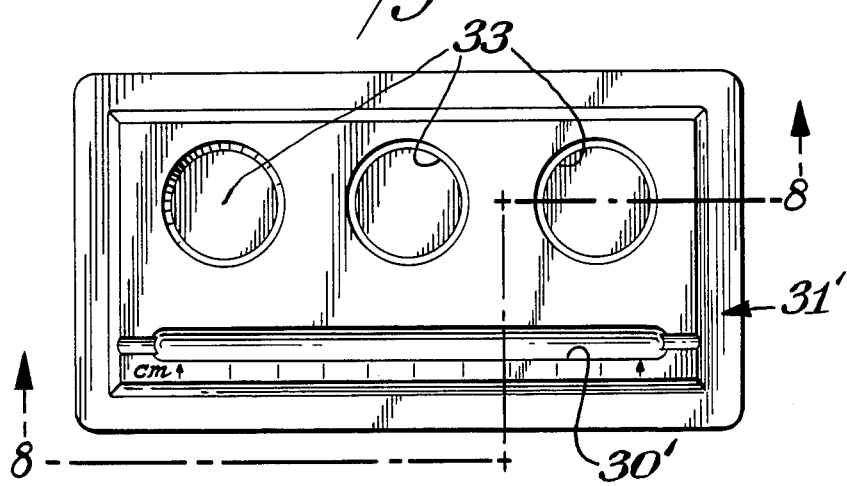
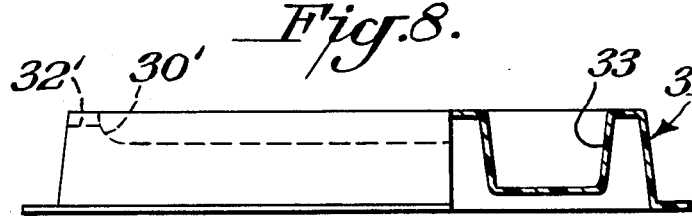 

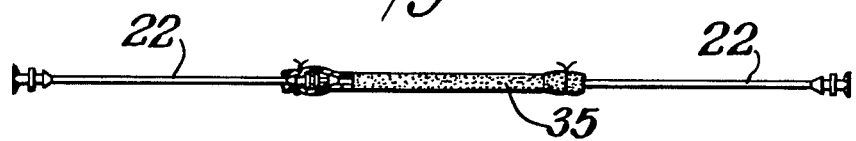
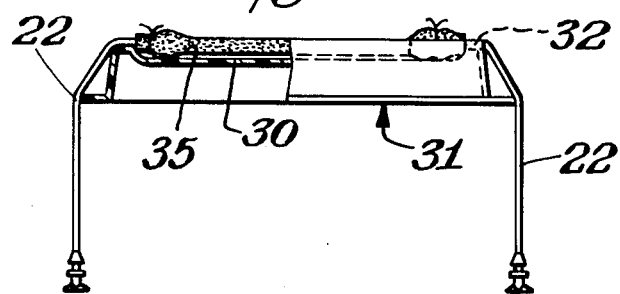
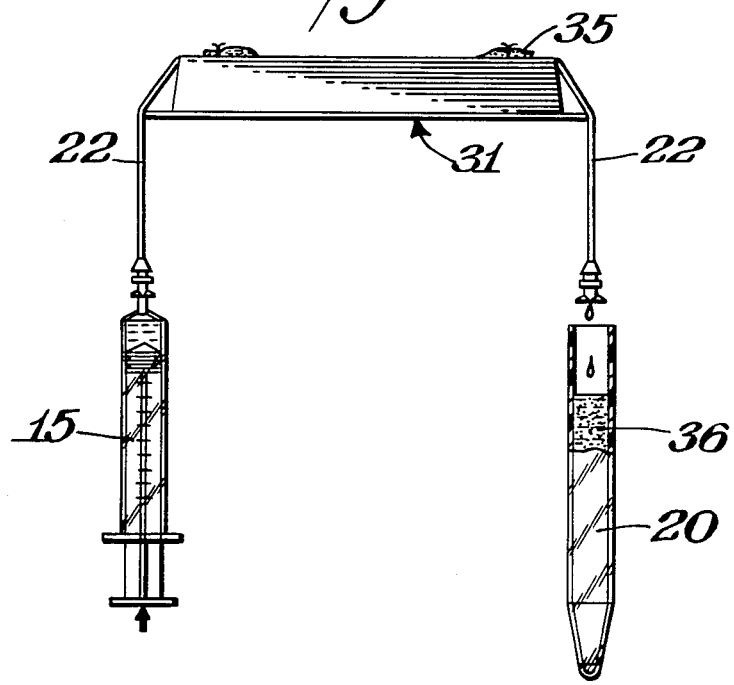
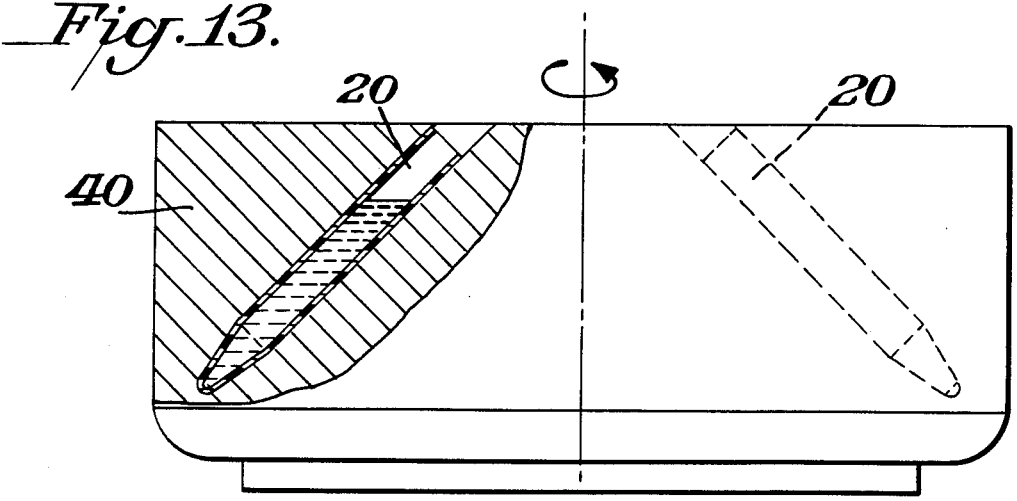

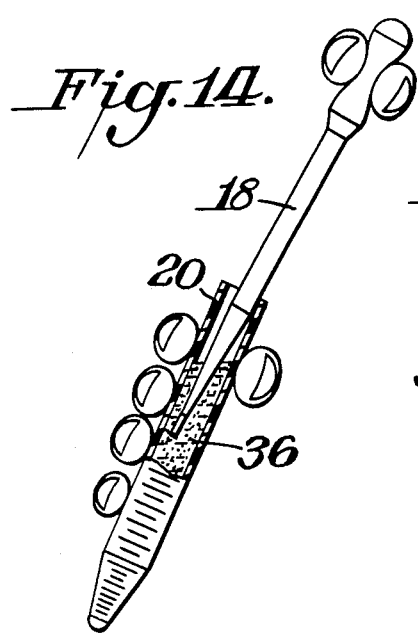
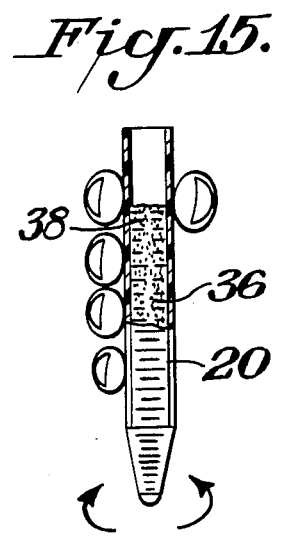
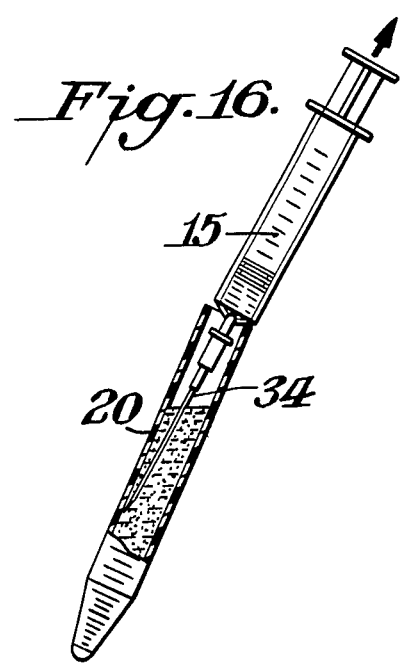
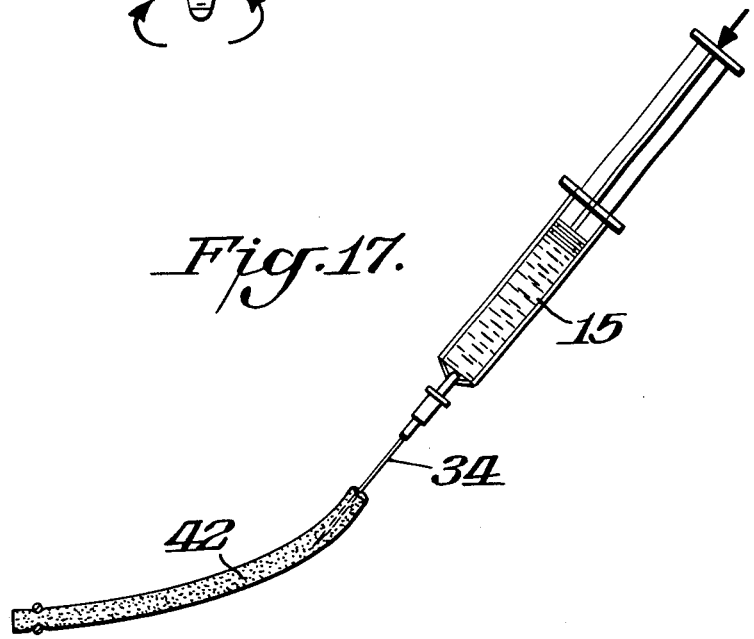

ENDOTHELIAL CELL HARVESTING KIT

BACKGROUND OF THE INVENTION

1. Field of the Invention

This invention relates to an endothelial cell harvesting kit which allows one to rapidly obtain viable human endothelial cells. Previous research efforts have been directed to develop antithrombogenic linings in synthetic vascular prostheses by endothelial cell seeding. In order to develop these linings, natural endothelial cells must first be extracted from segments of human arteries and veins.

2. Background of the Invention

Endothelial cell harvesting is a process for removing viable endothelial cells from a portion of autologous vein. Cell harvesting is accomplished by mechanical scraping or rubbing, or enzymatic treatment. One use for the harvested cells is to "seed" vascular prostheses.

Extensive animal experimentation and limited experience in humans indicate that seeded grafts endothelialize more quickly, induce less platelet reaction, and have better patency than nonseeded grafts. Adjunctive antiplatelet therapy may be required until the endothelial lining has developed. Antiplatelet therapy, however, is a standard procedure for patients receiving vascular grafts.

Briefly, harvesting is performed as follows. A segment of autologous vein is excised from a subject and the endothelial cells are removed. The cells so derived are concentrated by centrifugation, suspended in an aliquot of the subject's blood, and placed in the vascular graft until a thin layer of clot is formed on the graft wall. The "seeded" graft is immediately implanted in the subject. Endothelial cells "seeded" into the graft subsequently grow to confluence on the luminal surface thus providing the graft with a true neointima. Only autologous cells are used in this process.

Researchers at several universities have investigated methods of harvesting human cells for seeding. At the University of Indiana, a method was developed which involved the mechanical harvesting of canine endothelial cells. In those studies, endothelial cells were obtained by passing a steel wool pledget through excised vein segments. Mechanical harvesting methods have a derivation efficiency of less than about 75% and endothelial cells obtained in this manner are often contaminated with smooth muscle cells. (Herring, M. B. et al., "A Single-staged Technique For Seeding Vascular Grafts With Autogenous Endothelium." *Surgery*, 84:498–504 (1978)).

Another mechanical method for harvesting endothelial cells requires isolating a part of the aorta and placing it in sterile Hanks' Balanced Salt Solution (HBSS). The vessels were then further chemically treated, slit open and the endothelial cells were removed by gentle scraping with a scalpel blade. The collected cells were centrifuged and resuspended and further treated to suppress growth of contaminating smooth muscle cells (Sharefkin, J. et al., "Endothelial Cell Labeling With Indium-III-Oxine As A Marker of Cell Attachment To Bioprosthetic Surfaces." *Journal of Biomedical Materials Research*, 17:345–357 (1983)).

Another technique for harvesting human cells is by enzymatic means. Researchers at the University of Michigan used this method to obtain canine endothelial cells for seeding purposes. Here, cells were derived from segments of external jugular veins. According to this technique, freshly excised veins were secured and everted over a stainless steel rod and suspended in iced HBSS. The veins were then washed of any adherent blood cells by spinning with a centrifuge in fresh HBSS. After washing, the veins were incubated in a solution of tryspin, HBSS and ethylenediaminetetracetic acid (EDTA) and then a solution of collagenase, HBSS, calcium and magnesium. The vein with culture medium, enzyme, and wash solution were spun and centrifuged to obtain endothelial cells. (Graham, L. et al., "Expanded PTFE Vascular Prostheses Seeded With Enzymatically Derived And Cultured Canine Endothelial Cells," *Surgery*, 91:550–559 (1982)). Such enzymatic harvesting methods have a derivation efficiency between about 80 to nearly 100%. However, cells isolated by this method are often injured due to the required eversion of the vein.

Researchers at Harvard University have developed a technique where human saphenous veins are cannulated and then filled with collagenase and submerged in HBSS. The veins were then flushed several more times with collagenase. Dislodged cells were colleced by centrifugation. (Watkins et al., "Adult Human Saphenous Vein Endothelial Cells: Assessment Of Their Reproductive Capacity For Use In Endothelial Seeding Of Vascular Prosthesis, " *Journal of Surgical Research*, 36:588–596 (1984)).

Personnel at the University of Pennsylvania have also isolated endothelial cells from an umbilical vein by using a technique which included using a tapered glass cannula to which the vein was fastened. Initially, the vein was filled with collagenase and allowed to incubate. After incubation, one syringe was filled with medium 199 (M199) supplemented with antibiotics (gentamicin and amphotericin B). The syringes were pushed back and forth so that the vessel contents were similarly moved. The slight mechanical agitation promoted the release of endothelial cells that were subsequently centrifuged, resuspended and further treated for seeding. (Macarak, E. et al., "Adhesion of Endothelial Cells To Extracellular Matrix Proteins," *Journal Of Cellular Physiology*, 116:76–86 (1983)).

At Cornell University, techniques have also been developed to obtain endothelial cells from umbilical veins. That method required that the vein be cannulated at one end and flushed with HBSS. The other end was then cannulated and the vein was flushed with more HBSS. The vein was then filled with collagenase to distend it and incubated. After incubation, the cord was gently kneaded between the fingers up and down its length to increase cell yield. The collagenase solution was flushed out of the vein and centrifuged. The cells formed a pellet and they were resuspended for seeding. (Jaffe E., "Biology of Endothelial Cells," 1984, Martinus Nijhoff Publishers).

Researchers at Universitant Giessen have also investigated the use of Dispase I for isolating endothelial cells from the human umbilical cord vein. Here, human umbilical cords were flushed with Dulbecco-phosphate-buffered saline (D-PBS) to remove excess blood and then filled with Dispase I and incubated for 15 minutes. The vein was then flushed with D-PBS, centrifuged at room temperatures and the pellet was then resuspended for harvesting. (Thilo, D.G.S., et al., "Isolation Of Human Venous Endothelial Cells By Different Proteases," *Artery*, 8(3):259–266, 1980).

To date no reports averse to the seeding process or to the use of endothelial-cell-seeded grafts have appeared in the literature. In addition, no articles pertaining to the use of a kit for harvesting cells have been published.

SUMMARY OF THE INVENTION

A cell harvesting kit is provided comprising a packaging container containing three trays, a support holding the components needed for cell harvesting, and three vials containing enzyme, HBSS for reconstituting the enzyme, and HBSS for flushing and rinsing, respectively. The three trays include an outer tray having a lid sealingly engaged with the outer tray to preserve sterility of its contents, a component tray within the outer tray, the component tray having a sealed lid and having a shelf about its perimeter for supporting a support member having depressions therein for holding the components needed in cell harvesting, the component tray containing the third tray that comprises a process tray having a trough in which an excised vein may be placed for harvesting cells therefrom. The support member of the component tray of the cell harvesting kit further contains at least two disposable pipettes, two centrifuge tubes, two cannulae, two syringe tips in a case, and two syringe bottoms in a case.

In an alternate embodiment of the process tray, the trough is offset from the centerline of the process tray and three depressions are located therein in which the three vials are held in place.

A method for harvesting cells from a vein of a patient is also provided comprising the steps of excising a vein from the patient and placing the vein in the trough of the process tray and stretching the vein to its approximate in vivo length, flushing the vein with HBSS, filling the vein with neutral protease, allowing the neutral protease and cell solution to stand and transferring the solution to a centrifuge tube. Dispase I and II are preferably used as the neutral protease. The method steps for harvesting cells from a vein may be repeated.

BRIEF DESCRIPTION OF THE DRAWINGS

FIG. 1 shows a top plan view of the cell harvesting kit according to the present invention.

FIG. 2 shows a side elevational view, partly in cross-section, of the cell harvesting kit according to the present invention.

FIG. 3 is a side elevational view, partly in cross-section, of the cell harvesting kit taken along line 3—3 of FIG. 1 according to the present invention.

FIG. 4 is a top plan view of the process tray of the present invention.

FIG. 5 is a front elevation, partly in cross-section, of the process tray of the present invention taken substantially along line 5—5 of FIG. 4.

FIG. 6 shows an end elevational view of the process tray according to the present invention.

FIG. 7 shows a top plan view of an alternate embodiment of the process tray in which the trough for processing the vein is located to one side of the tray according to the present invention.

FIG. 8 shows a side elevational view of the alternate process tray according to the present invention, partly in cross-section, taken substantially along line 8—8 of FIG. 7.

FIG. 9 shows an end elevational view of the alternative process tray.

FIG. 10 shows the method step of cannulating the vein.

FIG. 11 shows the method step of mounting the vein and cannulae in the process tray.

FIG. 12 shows the method step of flushing the cells from the vein into a centrifuge tube.

FIG. 13 shows the method step of centrifuging the solution to form a pellet of cells at the bottom of the tubes.

FIG. 14 shows the method step of drawing off the supernatent with the pipette after centrifugation.

FIG. 15 shows the method step of resuspending the cells in a small amount of blood.

FIG. 16 shows the method step of drawing the blood-cell mixture into the syringe.

FIG. 17 shows the method step of injecting the blood-cell mixture into a graft.

DETAILED DESCRIPTION OF THE PREFERRED EMBODIMENTS

A cell harvesting kit and a method for harvesting cells from a vein are provided.

The present invention provides an endothelial cell harvesting kit wherein a combination of components needed for harvesting, enzymes, and salt solutions are brought together for easy access in the harvesting of cells from veins. This kit may be used directly in the operating room and the harvesting of cells may occur during an operation. The preferred temperature of the solutions used during harvesting is in the range from about 20° C. to about 37° C. The temperature may be maintained by a supplementary heating element not provided in the kit. The neutral protease enzymes that may be used in this kit and with this method include Dispase I and Dispase II.

In the cell harvesting kit, a rectangular container having a sealed lid and containing three trays and a support member is provided. The three trays include a generally rectangular process tray having a longitudinal trough in which a vein is to be placed for cell harvesting contained within a component tray having a molded support in which a plurality of depressions are located for utensils used in cell harvesting such as pipettes, cannulae, syringes, needles, and centrifuge tubes, all contained within an outer tray hermetically sealed for maintaining sterility of the component tray and the process tray contained within. In an alternative embodiment of the process tray, a plurality of depressions are located in the process tray in which are placed the vials containing neutral protease and salt solutions and the trough in which a vein is to be placed for cell harvesting is offset from the center line of the tray.

A detailed description of the invention and preferred embodiments is best provided with reference to the accompanying drawings wherein FIG. 1 is a top plan view of the cell harvesting kit 10. The kit is comprised of three trays contained in a packaging container 11. The three trays include an outer tray 12 having a lid 13, a component tray 14 having a support 16 and lid 17, and a process tray 31. Preferably lids 13 and 17 are transparent plastic. As depicted in FIG. 1, the support member 16 contains depression 19, 21, 23, 25, and 27 designed to hold components needed in harvesting of cells. The following components are found within this support member 16: two disposable pipettes 18 located in depression 19, two 1.5 ml centrifuge tubes 20 located in depression 21, two cannulae 22 in depressions 23, two syringe needle cases 24 containing needles 34 located in depression 25, and two syringe cases 26 containing syringes 15 located in depression 27. A longitudinal depression 29 provides easy access to the various components by the person using the kit.

Three vials 28 are located outside of the support member 16, component tray 14, and outer tray 12 but within the container 11. The three vials contain the neutral protease enzyme, HBSS for reconstituting the enzyme, and HBSS for rinsing the vein and cells, respectively.

FIG. 2 is a side elevational view, partly in cross-section, of the kit 10 according to the present invention. The container 11 is shown to contain three spearate trays that include an outer tray 12, a component tray 14 having a support member 16, and a process tray 31 having a trough 30. The three vials 28 are located within container 11 but outside the trays 12, 14, and 31.

The components are placed within the support member 16 so that the head of one component is adjacent to the bottom of the similar component within the specific depression for the component. Thus, for example, the pipettes 18 viewed in FIG. 2 show the head of one pipette and the bottom of the other. Also shown in the support member 16 of FIG. 2 are the depressions with corresponding components including depressions 19 containing pipettes 18, depressions 21 containing centrifuge tubes 20, depressions 23 containing cannulae 22, and depressions 27 containing cases for syringes 26.

FIG. 3 is a side elevational view, partly in cross-section, of the kit 10 taken along line 3—3 of FIG. 1. FIG. 3 shows container 11 containing outer tray 12, component tray 14 having support member 16 therein, and process tray 31. A side view of centrifuge tube 20 is shown within depression 21 within support member 16.

FIG. 4 is a top plan view of the process tray 31. A trough 30 in which the vein is to be placed is located within the center of the process tray 31. At either end of trough 30 are located slots 32 for accepting the cannulae.

FIG. 5 is a front elevation, partly in cross-section of the process tray 31 taken substantially along line 5—5 of FIG. 4. A trough 30 is located within the center of the process tray 31. At either end of trough 30 are located slots 32.

FIG. 6 shows an end elevational view of the process tray 31, trough 30, and slot 32.

FIGS. 7, 8, and 9 show an alternative embodiment of the process tray 31'. FIG. 7 shows a top plan view of the process tray 31' in which the trough 30' for the vein is located to one side of the tray rather than in the center of the tray. There are also three depressions 33 within the tray 31' for holding the vials 28. At either end of trogh 30' are located slots 32' for accepting cannulae.

FIG. 8 shows a front elevational view of this alternative process tray partly in cross-section, taken substantially along lines 8—8 of FIG. 7. A trough 30' and depression 33 within the tray 31' are shown.

FIG. 9 shows an end elevational view of the tray with both a trough 30' and a depression 33 for a vial 28.

Components which may also be needed but are not part of the kit include one clinical centrifuge capable of providing a centrifugal force of 300 times gravity with a rotor to accept 15 ml tubes, one heat block to warm the tray, and one valvulotome.

Modifications may be made in the design of the container and trays, the packaging of the enzyme and HBSS, the number and size of the syringes, the number of pipettes, the number of centrifuge tubes, and/or the method of cell collection after harvesting.

FIGS. 10 through 17 shows the method steps undertaken in the use of the kit to harvest endothelial cells. Generally, to use the kit, while a patient is being prepared for vascular reconstructive or bypass surgery, a small segment of vein 35 is removed. As depicted in FIG. 10, the removed vein is cannulated with the cannulae 22 at each end of the vein. As shown in FIG. 11, the vein 35 and cannulae 22 are then mounted in the process tray 31 within the trough 30. The lumen of the vein is gently rinsed by flushing with HBSS. If obstructive valves are encountered, they are to be cut with a valvulotome. The vein is filled with the reconstituted neutral protease preferably Dispase. After five minutes, the enzyme solution is withdrawn and replaced with fresh enzyme. Ten minutes later, the vein 35 is again drained. Both collections of enzyme solution are combined in one of the centrifuge tubes 20 as shown in FIG. 12.

The vein is then rinsed with HBSS which is collected and divided between both centrifuge tubes 20. After equalizing solution levels in the two tubes with HBSS, the solutions are centrifuged in a centrifuge 40 at 300 times gravity for three minutes as shown in FIG. 13. A pellet should be visible at the bottom of one or both trays after centrifugation.

As shown in FIG. 14, the supernatent is carefully aspirated from over the cell pellet in the centrifuge tube 20 containing the enzyme solutions with a pipette 18. Fresh HBSS is poured intot the tube 20 and the cells are resuspended by gentle agitation. The supernatent in the second tube 20 is also carefully aspirated, and the cell pellet is resuspended in the cell suspension of the first tube 20 by gentle agitation. One drop of the cell suspension is removed and placed on the microscope slide so that the presence of cells may be confirmed.

Twenty minutes prior to graft implantation, 10 to 20 ml of nonheparinized blood are withdrawn from the patient. A small amount of fresh nonheparinized blood is mixed with the cell suspension in the first tube 20 as shown in FIG. 15. This step is done immediately before seeding the vascular graft 42.

A small amount of nonheparinized blood is also used to coat the inner surface of the vascular graft 42. This is done by closing one end of the graft with an atraumatic clamp and injecting the blood into the graft. The graft is gently massaged to completely coat the inner surface. After five minutes, any excess blood is poured out of the graft. Next, the blood-cell suspension is drawn into syringe 24 as shown in FIG. 16 and is then injected into the graft as shown in FIG. 17 and the open end clamped. The blood-cell suspension is distributed over the surface of the graft by gentle tipping, turning, and massaging.

Modifications of the kit may be made to improve the ease of handling of the vein and endothelial cells, increase the yield of endothelial cells, and/or reduce the time required for cell harvesting and seeding.

While the invention has been disclosed herein in connection with certain embodiments and detailed descriptions, it will be clear to one skilled in the art that modification or variations of such details can be made without deviating from the gist of the invention and such modifications or variations are considered to be within the scope of the claims herein below.

We claim:

1. A cell harvesting kit comprising: a packaging container containing three trays, a support holding the components needed for cell harvesting and three vials, said vials containing enzyme, HBSS for reconstituting the enzyme and HBSS for flushing and rinsing, respectively, said three trays comprising:
(a) an outer tray having a lid sealingly engaged with said outer tray to preserve sterility of its contents;
(b) a component tray within said outer tray, the component tray having a sealed lid and having a shelf about its perimeter for supporting a support member having depressions therein for holding said components needed in cell harvesting, said component tray also containing the third of said three trays, said third tray comprising;

(c) a process tray having a trough in which an excised vein may be placed for harvesting cells therefrom.

2. The cell harvesting kit of claim 1 in which said support member contains at least two disposable pipettes, two centrifuge tubes, two cannulae, two syringe tips and two syringe bottoms.

3. The cell harvesting kit of claim 1 wherein said trough in said process tray is offset from the centerline of the process tray and said process tray has three depressions therein in which said three vials are held in place.

* * * * *

UNITED STATES PATENT AND TRADEMARK OFFICE
CERTIFICATE OF CORRECTION

PATENT NO. : 4,736,850

DATED : April 12, 1988

INVENTOR(S) : Phillip B. Bowman; David M. Workinger; John L. Fisher

It is certified that error appears in the above-identified patent and that said Letters Patent is hereby corrected as shown below:

In col. 2, line 58, please change "Universitant" to —Universitat—.

In col. 3, lines 66-67, please change "alternative" to —alternate—.

In col. 5, line 11, please change "spearate" to —separate—.

In col. 5, line 52, please change "trogh" to —trough—.

In col. 6, line 29, please change "intot" to —into—.

Signed and Sealed this

Second Day of August, 1988

Attest:

DONALD J. QUIGG

*Attesting Officer*  *Commissioner of Patents and Trademarks*